(12) United States Patent
Lavender et al.

(10) Patent No.: US 9,310,333 B2
(45) Date of Patent: Apr. 12, 2016

(54) METHODS OF ANALYZING PLAQUE

(75) Inventors: Stacey Lavender, Chesterfield, NJ (US); R. Peter Santarpia, III, Edison, NJ (US); Richard J. Sullivan, Atlantic Highlands, NJ (US)

(73) Assignee: Colgate-Palmolive Company, New York, NY (US)

( * ) Notice: Subject to any disclaimer, the term of this patent is extended or adjusted under 35 U.S.C. 154(b) by 305 days.

(21) Appl. No.: 13/985,017

(22) PCT Filed: Feb. 11, 2011

(86) PCT No.: PCT/US2011/024420
§ 371 (c)(1),
(2), (4) Date: Aug. 12, 2013

(87) PCT Pub. No.: WO2012/108871
PCT Pub. Date: Aug. 16, 2012

(65) Prior Publication Data
US 2013/0323185 A1    Dec. 5, 2013

(51) Int. Cl.
*G01N 27/447*   (2006.01)
*A61C 19/04*    (2006.01)

(52) U.S. Cl.
CPC ............. *G01N 27/447* (2013.01); *A61C 19/04* (2013.01)

(58) Field of Classification Search
CPC ............................ G01N 27/447; A61C 19/04
See application file for complete search history.

(56) References Cited

FOREIGN PATENT DOCUMENTS

| CN | 1952167 | 4/2007 |
|---|---|---|
| EP | 0442315 | 8/1991 |
| JP | 2007-099632 | 4/2007 |
| JP | 2008-512104 | 4/2008 |
| WO | WO 98/03185 | 1/1998 |
| WO | WO 2009/100262 | 8/2009 |
| WO | WO 2009/100275 | 8/2009 |

OTHER PUBLICATIONS

Gao et al., "A Study of Oral Health Condition in Individuals with No Oral Hygiene and its Association with Plaque Acidogenesis," The Chinese Journal of Dental Research, vol. 3, No. 2, 2000, pp. 44-48.*
article entitled "Storing bacterial samples for optimal viability" published by Thermo Scientific, publication date unkown, downloaded Aug. 7, 2015.*
Dong Yang Mei et al., Effect Of Composition In Plaque Fluid On Evaluation Of Individual Caries Risk. Chinese Journal of Stomatology, Jul. 1, 2001, vol. 36, No. 4, pp. 277-280.
Damen et al., Acidogenicity of buccal plaque after a single rinse with amine fluoride—stannous fluoride mouthrinse solution, Caries Research, 2002; 36: 53-57.
Francois et al., Effect of the concentration of 18-crown-6 added to the electrolyte upon the separation of ammonium, alkali and alkaline-earth cations by capillary electrophoresis, Journal of Chromatography, vol. 706, No. 1, Jul. 7, 1995.
Gerardu et al, Plaque formation and lactic acid production after the use of amine fluoride/stannous fluoride mouthrinse, European Journal of Oral Sciences. 2007; 115: 148152.

(Continued)

*Primary Examiner* — Alex Noguerola

(57) ABSTRACT

The invention provides a method of measuring ammonia and/or calcium in a sample of dental plaque, comprising obtaining the sample of plaque and measuring ammonium and calcium ions using capillary electrophoresis, together with methods of diagnosis, treatment and screening based on evaluation of plaque.

18 Claims, 2 Drawing Sheets

(56) References Cited

OTHER PUBLICATIONS

Gerardu et al., The Effect of a Single Application of 40% Chlorhexidine Varnish on the Numbers of Salivary Mutans Streptococci and Acidogenicity of Dental Plaque, Caries Research. 2003; 37: 369-373.

International Search Report and Written Opinion of the International Searching Authority issued in International Application PCT/US2011/024420 mailed Nov. 3, 2011.

Jackson et al., Capillary electrophoresis of inorganic ions and low-molecular-mass ionic solutes, Trac, Trends in Analytical Chemistry, vol. 12, No. 6, 1 Jun. 1993, 231-238.

Kallio-Pantsar et al., Determination of sodium, potassium, calcium and magnesium cations by capillary electrophoresis compared with ion chromatography, Analytica Chimica Acta. 1995; 314: 67-75.

Margolis, et al., Composition of Pooled Resting Plaque Fluid From Caries-Free and Caries-Susceptible Individuals, Journal of Dental Research, vol. 67, No. 12, 1 988, pp. 1468-14 75.

Shi et al., New electrolyte systems for the determination of metal cations by capillary zone electrophoresis. Journal of Chromatography A. 1994: 671: 429-435.

Warren, C.R. and M.A. Adams. Simultaneous analysis of the major metal cations and ammonium by CZE. Phytochemical Analysis. 2004; 15: 407-413.

Written Opinion of the International Preliminary Examining Authority issued in International Application PCT/US2011/024420 mailed Feb. 5, 2013.

Xu et al., 2004, "The Association of Amino Acid with Caries Susceptibility in Dental Plaque Fluid of 3 - 5 - year - old Children" J. Oral Sci. Res. 20(6):619-622 (Abstract only in English).

Hirokawa et al., 2007, "Simultaneous monitoring of inorganic cations, amines and amino acids in human sweat by capillary electrophoresis," Analytica Chimica Acta 581(1):83-88.

Margolis et al., 1994, "Composition and cariogenic potential of dental plaque fluid," Critical Review Oral Biology Medicine 5(1):1-25.

Hopper et al., "A novel method for analysis of explosives residue by simultaneous detection of anions and cations via capillary zone electrophoresis," Talanta, Aug. 2005, 67(2):304-12.

Mori et al., "Use of phosphobetaine-type zwitterionic surfactant for the determination of alkali and alkaline earth metal ions and ammonium ion in human saliva by capillary electrophoresis," Anal. Bioanal Chem, Sep. 2002, 374(1):75-9.

* cited by examiner

METHODS OF ANALYZING PLAQUE

FIELD OF THE INVENTION

This invention relates to methods for detecting ammonia, calcium and acids in plaque using capillary electrophoresis.

BACKGROUND OF THE INVENTION

In the initial progression of dental caries, certain bacteria in the oral cavity metabolize sugar to make organic acids as a product. Some of these organic acids include formic acid, succinic acid, butyric acid, proprionic acid, acetic acid and lactic acid. It is the proximity of this acidogenic bacteria to the tooth surface and the contact of the acid with the surface that eventually causes a breakdown of enamel or demineralization. The frequency of this production and the longer the contact with the enamel, the greater degree of demineralization for the eventual progression to a caries lesion. Lactic acid in particular is increased after plaque is exposed to a sucrose challenge and has been shown to be one of the more detrimental acids produced for the demineralization of the tooth.

Not all bacteria in the oral cavity are cariogenic or otherwise damaging, however. The type of bioflora in the mouth plays a significant role in the development of cavities and in oral health generally. For example, arginine and other basic amino acids have been proposed for use in oral care and are believed to have significant benefits in combating cavity formation and tooth sensitivity. It has been hypothesized that a significant factor in the beneficial effect of arginine is that arginine and other basic amino acids can be metabolized by certain types of bacteria, e.g., *S. sanguis*, which are not cariogenic and which compete with cariogenic bacteria such as *S. mutans*, for position on the teeth and in the oral cavity. The arginolytic bacteria can use arginine and other basic amino acids to produce ammonia, thereby raising the pH of their environment, while cariogenic bacteria metabolize sugar to produce lactic acid, which tends to lower the plaque pH and demineralize the teeth, ultimately leading to cavities.

In developing new compositions and methods for oral care, it may be desirable to focus on inhibiting, destroying or discouraging particularly those bacteria that cause the damage, rather than simply using methods that kill all bacteria, and/or to focus on methods that neutralize or disperse the damaging acids.

Capillary electrophoresis, e.g. capillary zone electrophoresis, separates ionic species by charge, frictional forces and hydrodynamic radius. In traditional electrophoresis, electrically charged analytes move in a conductive liquid medium under the influence of an electric field. Capillary electrophoresis separates ions based on their size to charge ratio in the interior of a small capillary filled with an electrolyte.

Capillary electrophoresis has been used to measure acids in plaque. See, e.g., Damen J. J. M., et al. Caries Research (2002) 36: 53-57. WO 2009/100262 (incorporated herein by reference) discloses monitoring of both acid and ammonia in plaque, but the methods for measuring ammonia, adapted from a plasma diagnostic kit, are time consuming, taking about a week to complete. Also this method is not suitable for high-throughput use.

In studying plaque formation and tooth decay, and in developing new compositions and methods for oral care, therefore, it would be useful to have a simple, fast, easy-to-use method to measure ammonia production and optionally also acidification of plaque, which can allow one to assess the presence and activity of beneficial and optionally also cariogenic bacteria in the plaque, as well as to assess the disease state of the patient, and the effectiveness of oral care compositions and methods. It would be moreover be useful to have more efficient ways to monitor the type of bioflora in the mouth, e.g., to determine the optimal treatment and to monitor the effectiveness of treatment.

SUMMARY OF THE INVENTION

The invention provides a simple, easy-to-use method for measuring ammonia and/or calcium, and optionally acids, in a plaque sample. The method is useful for high-throughput use in development of improved oral care products and methods, as well as diagnostic and therapeutic methods. The method comprises obtaining a sample of plaque and measuring ammonia and/or calcium, and optionally acids, using capillary electrophoresis. For example, in one embodiment, the method (Method 1) comprises the steps of
  a. Obtaining a sample of plaque;
  b. Diluting the sample with water;
  c. Heating the sample, e.g., sufficiently to kill bacteria and release ions into solution;
  d. Isolating the liquid fraction of the sample, e.g. using centrifugation and/or filtration;
  e. Combining the liquid fraction with
     i. An agent allows electrophoretic separation of magnesium ions from calcium ions, e.g. hydroxyisobutyric acid,
     ii. an agent that allows electrophoretic separation of potassium ions from ammonium ions, for example 18 crown 6 ether,
     iii. A buffer, comprising a basic agent, e.g., imidazole, and an acidic agent, which may be optionally the same as one of the complexing agents i or ii, e.g., hydroxyisobutyric acid, e.g., to buffer the liquid to about pH 4-5, e.g. about pH 4.3;
  f. Passing the product of step e through a capillary tube, wherein there is an electric potential between one end of the capillary tube and the other sufficient to induce electrophoretic flow of ions through the tube;
  g. Detecting ammonium ions and/or calcium ions in liquid that has passed through at least a portion of the capillary tube, e.g., using ultraviolet or ultraviolet-visual absorbance, mass spectroscopy, surface enhanced Raman spectroscopy, or other detection means.

Method 1 thus includes the following methods
  1.1. Method 1 wherein in step a the plaque is obtained from a human patient;
  1.2. Method 1 or 1.1 wherein in step b the plaque is diluted to a concentration of about 0.01-0.1 mg plaque/ml water, e.g., about 0.03-0.04 mg plaque/ml water;
  1.3. Any of the foregoing methods wherein in step c, the sample is heated to 60°-95° C., e.g. about 80° C., then cooled to less than 10° C., e.g. about 4° C.;
  1.4. Any of the foregoing methods wherein in step d, the liquid fraction is isolated by centrifuging the sample, removing the supernatant thus obtained, and filtering the supernatant;
  1.5. Any of the foregoing methods wherein in step e, the agent that allows electrophoretic separation of magnesium ions from calcium ions is selected from hydroxyisobutyric acid, lactic acid, malonic acid, and tartaric acid;
  1.6. The foregoing method wherein in step e, the agent that allows electrophoretic separation of magnesium ions from calcium ions is hydroxyisobutyric acid;
  1.7. Any of the foregoing methods wherein in step e, the agent that allows electrophoretic separation of potassium ions from ammonium ions is selected from neutral crown ethers and cyclofructans;

1.8. The foregoing method wherein in step e, the agent that that allows electrophoretic separation of potassium ions from ammonium ions is 18 crown 6 ether;

1.9. Any of the foregoing methods wherein in step e, the buffer comprises an organic base;

1.10. Any of the foregoing methods wherein in step e, the buffer comprises imidazole;

1.11. Any of the foregoing methods wherein in step e, the liquid fraction is combined with imidazole (e.g. about 5-7 mM, e.g. about 6 mM), hydroxyisobutyric acid (e.g., about 1-2 mM, e.g. about 2.5 mM), and 18 crown 6 ether (e.g. about 2-3 mM, e.g., about 2.5 mM);

1.12. Any of the foregoing methods wherein in the product of step e, the pH is about 4-5, e.g. about pH 4.3;

1.13. Any of the foregoing methods wherein in step f, the electric potential is about 5-30 kV;

1.14. Any of the foregoing methods wherein in step g, the means of detection is UV-Vis absorption.

Method 1 may optionally further provide measuring acid in the plaque sample, for example, Method 1 comprising the additional step of using capillary electrophoresis to measure the acid in the plaque sample; for example, Method 1 comprising the following additional steps:

h. Separating the liquid fraction obtained by step d into a first portion and a second portion, i. Carrying out steps e, f, and g on the first portion, j. Combining a buffer with the second portion, e.g., 2,6 pyridine dicarboxylic acid and hexadecyltrimethyl ammonium bromide, e.g., to about pH 5-6, e.g., about pH 5.66, k. Passing the product of the preceding step through a capillary tube, wherein there is an electric potential between one end of the capillary tube and the other sufficient to induce electrophoretic flow of ions through the tube;

l. Detecting acid anions, e.g., lactate, succinate, acetate, and/or proprionate anions, e.g. lactate ions, in liquid that has passed through at least a portion of the capillary tube, e.g., using ultraviolet or ultraviolet-visual absorbance, mass spectroscopy, surface enhanced Raman spectroscopy, or other detection means.

In another embodiment, the invention measures plaque ammonia production levels to determine the relative population of arginolytic bacteria, and optionally additionally measures plaque lactic acid levels to determine the relative population of cariogenic bacteria.

In another embodiment, the invention quantifies levels of at least one arginolytic bacteria, e.g., *S. sanguis*, and optionally at least one cariogenic bacteria, e.g., *S. mutans*, and e.g., using one or more of the following techniques, e.g., as described in WO 2009/100262 (incorporated herein by reference):

a. the polymerase chain reaction (PCR), for example quantitative real time PCR, to characterize the bioflora in the mouth, e.g., in the plaque or saliva;

b. reverse transcriptase PCR (RT-PCR) to characterize the bioflora in the mouth, e.g., in the plaque or saliva; and or c. antibody probes, e.g., fluorescent antibody probes are used to characterize the bioflora in the mouth, e.g., in the plaque or saliva.

In another embodiment, a plaque sample from a patient is assessed using one of the foregoing methods, and treatment prescribed accordingly. For example, the methods of the invention are particularly useful to detect potentially damaging changes in plaque ecology and to allow corrective treatment before there is measurable or significant demineralization or damage to the teeth.

The invention thus provides methods to enhance oral health, e.g., to reduce plaque accumulation; treat, relieve or reduce dry mouth; whiten teeth; enhance systemic health, including cardiovascular health, e.g., by reducing potential for systemic infection via the oral tissues; immunize the teeth against cariogenic bacteria and their effect; clean the teeth and oral cavity and/or reduce erosion of the teeth, the method comprising measuring the bioflora of the oral cavity, e.g., using any of the foregoing methods, e.g., Method 1, et seq., and if indicated, administering an oral care product comprising an effective amount of a basic amino acid or salt thereof, e.g., arginine.

The invention further provides the use of a basic amino acid, in free or salt form, for the manufacture of medicament for enhancing oral health in a subject whose oral cavity bioflora comprise elevated levels of cariogenic bacteria and/or elevated lactate levels, and/or low levels of arginolytic bacteria and/or low levels of plaque ammonia production, as measured by a method according to the present invention, e.g., Method 1, et seq.

The invention further provides a method for cosmetically enhancing the oral cavity (wherein such cosmetic enhancement may include e.g. making teeth whiter and/or reducing halitosis) which method comprises measuring the bioflora of the oral cavity using a method according to the present invention, e.g., Method 1, et seq., and if indicated by the presence of elevated levels of cariogenic bacteria and/or elevated lactate levels, and/or the presence of low levels of arginolytic bacteria and/or low levels of plaque ammonia production, administering an oral care product comprising a basic amino acid in free or salt form.

The invention further provides a method for assessing the efficacy of an oral care composition in promoting arginolytic bacteria and optionally inhibiting cariogenic bacteria comprising measuring ammonium levels in plaque using the method of Method 1, et. seq.

DETAILED DESCRIPTION OF INVENTION

Figure 1:
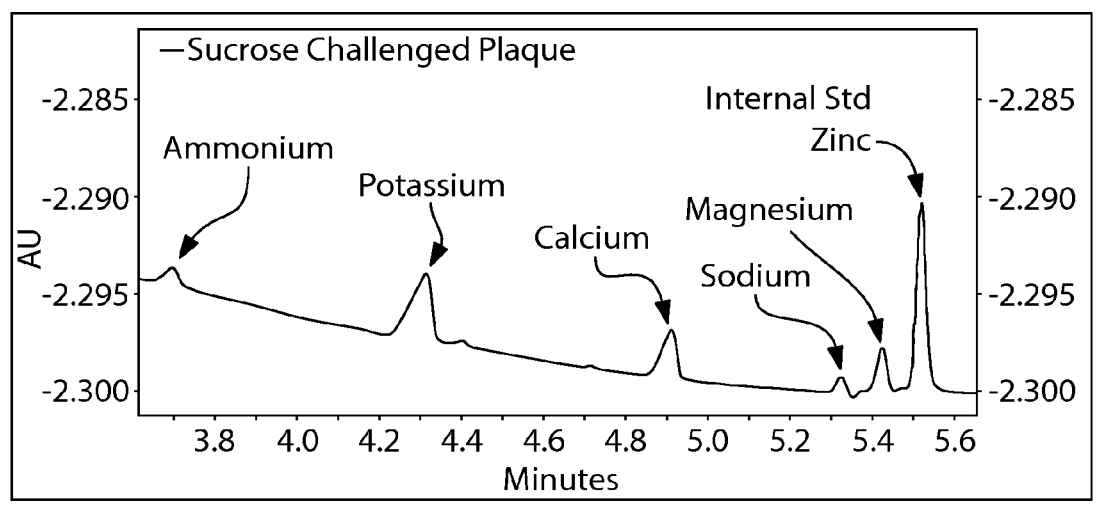
FIG. 1 is a UV absorbance spectrum for a sample of plaque following sugar challenge, measuring cations, e.g. ammonium and calcium.

The ability of dental plaque to convert arginine to ammonia is a marker of arginolytic activity. Certain bacteria have the ability to convert arginine to ammonia, just as certain bacteria can convert sugars to acid. It is beneficial to increase the relative concentration of arginolytic species because these bacteria create conditions that are unfavorable for proliferation of cariogenic bacteria, which favor acidic conditions and increase caries risk. Daily use of arginine is expected to create a shift in the plaque ecology that favors arginolytic bacteria in an analogous manner that frequent consumption of sugar creates conditions that favor acid producing bacteria. Ammonia is a base that is capable of neutralizing acids and helps maintain neutral plaque pH. Neutral pH conditions are more favorable to nonpathogenic bacteria. Measurement of ammonia production measures the contribution from all the bacteria capable of converting arginine to ammonia. This method is thus in some respect superior to other approaches for evaluating plaque bioflora, such as real time PCR method (further described below), which measure concentration of select arginolytic bacteria and do not distinguish between metabolically active (live) and inactive (dead) bacteria.

Just as the measurement of ammonia levels serves as a proxy to measure the levels of arginolytic bacteria, lactic acid serves as a proxy to measure the levels of cariogenic bacteria. Accordingly, it may be of interest to measure both ammonium and lactate from the same sample.

The main separation modes used in capillary electrophoresis include capillary zone electrophoresis, micellar electrokinetic capillary chromatography, capillary isotachophoresis, capillary gel electrophoresis, and capillary isoelectric focusing. In a particular embodiment, the invention uses capillary zone electrophoresis. Generally, the flow in the capillary is from anode to cathode, so cations tend to migrate through the capillary faster than the electro-osmotic flow, while anions are slowed by their charge, and come through more slowly. Analytes having similar charge and size can be separated using larger compounds that tend to complex more strongly with one ion than another, thereby allowing separation.

For example, potassium and ammonium have similar electrophoretic mobility in an imidazole electrolyte system. Separation is possible, however, with the addition of a neutral crown ether, e.g. 18 crown 6 ether, or a cyclofructan. Such compounds form a complex with potassium, increasing its size and slowing down its migration time. This results in two distinct migration times for ammonium and potassium allowing for peak identification and quantification or ammonium.

Calcium and magnesium also co-migrate a weak chelator such as hydroxyisobutyric acid (HIBA) allows separation of these ions. Also, HIBA changes the migration order of sodium and calcium. When no HIBA is added, sodium migrates before calcium. When the complexing agent is added the order is reversed. This is advantageous because when sodium migrates first and is in a large concentration it can overlap with the calcium peak, leaving the calcium peak undetected. See electropheragram in FIG. 1. Thus, this is also a useful tool and method to detect if calcium is being delivered from an oral care product or, inversely, if calcium is being lost by tooth mineral in demineralization.

In one embodiment, the buffer system used for capillary electrophoresis analysis of ammonium and calcium levels comprises imidazole, hydroxyisobutyric acid, and 18 crown 6 ether. This system thus includes two complexing agents to optimize and separate peak migration.

Example 1

Ammonium and Calcium in Plaque

Subjects have plaque taken without morning oral hygiene and without eating or drinking from the previous evening. They rinse with a 10% sucrose solution for 2 minutes. After 8 minutes, plaque is collected by scraping the tooth surface(s). Plaque samples are collected on ice in preweighed tubes, and the plaque weight is determined. The concentration is normalized using ultra-pure water. The plaque is diluted to a final approximate concentration of approximately 0.03-0.04 mg of plaque/mL of water and spun down in the water for 30 seconds at 4° C. The plaque is then vortexed into solution and then heated to 80° C. for 5 minutes to kill bacteria and release the ions into solution. The plaque is then placed in an ice/water bath for an additional 5 minutes. The plaque solution is then centrifuged for 15 minutes at 13,000 rpm at 4° C. The supernatant is quickly removed and filtered by a 0.2 micron Nylon centrifugal filter for 3 minutes at 12,000 rpm at 4°. The supernatant is then either analyzed by capillary electrophoresis or stored at −80°. The buffer system used for capillary electrophoresis analysis is 10 mM imidazole, 6.0 mM hydroxyisobutyric acid, 2.5 mM 18 crown 6 ether, pH 4.3.

FIG. 1 is an example of capillary electrophoretic analysis of plaque following sugar challenge using this method.

Example 2

Acid in Plaque

Figure 2:
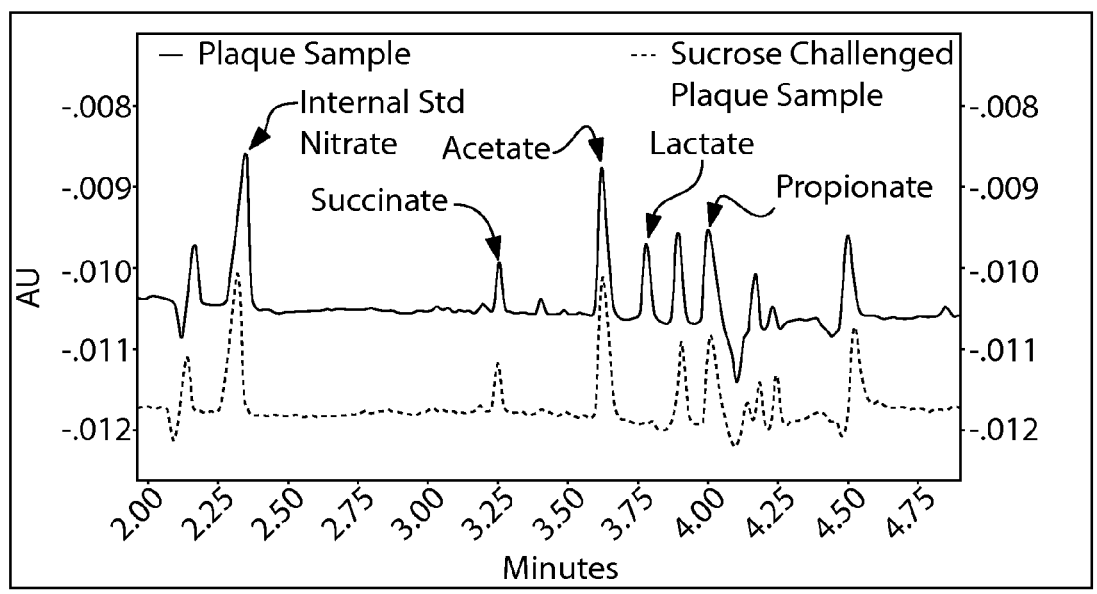
FIG. 2 is a UV absorbance spectrum for a sample of plaque following sugar challenge and control, measuring acid anions.

The plaque sample is prepared as in example 1. The buffer system used is different: 20 mM 2,6 pyridine dicarboxylic acid and 0.5 mM hexadecyltrimethyl ammonium bromide, pH 5.66. FIG. 2 is an example of capillary electrophoretic analysis of plaque, control and after sugar challenge, using this method.

In addition to measuring lactic acid in plaque, this method also measures succinic, acetic and proprionic acids in plaque. These organic acids are also important in the process of caries and in subsequent lesion formation. Since organic acids have little or no ultraviolet (UV) absorbance, detection is accomplished using 2,6-pyridine dicarboxylic acid as a background electrolyte (BGE). In this indirect detection method, the BGE has strong UV absorptive properties and produces a high background absorption in the UV detector. In the absence of non-absorbing analytes, the background signal is constant. When ionic analytes are introduced, they displace UV absorbing additive ions on a charge-to-charge basis, resulting in a negative peak relative to the high UV absorption baselines. With the analysis, the sample is injected by pressure for 10 seconds at 0.5 psi. The separation is performed at −25 kV and the capillary is thermostated at 25° C. The wavelength for indirect UV detection is selected at 254 nm, and the signal with negative peaks is inverted to obtain a more familiar electropherogram to integrate and process. To correct for injection errors, each sample is run with the incorporation of a 1.5 mM sodium nitrate internal standard, and a calibration curve was constructed using sodium lactate standards (Sigma, St. Louis, Mo., USA). Based upon the ratio of (lactate/nitrate) peak area and the initial plaque weight, the concentration of lactate present in plaque sample is determined.

A clinical study is also performed to test the validity of this methodology. The objective of the study is to evaluate the methodology developed to measure acid production in plaque samples by exposing plaque to a known acid reducer, chlorhexidine. This study is a monadic design. 6 subjects who meet the inclusion/exclusion criteria are enrolled in the study. Following enrollment, subjects use Colgate MaxFresh for one week. After the washout period, subjects rinse with water for 30 seconds for baseline evaluation. After an elapsed time of 30 minutes subjects rinse with a 10% sucrose solution for 2 minutes, followed by plaque collection 8 minutes later. Forty eight hours later subjects come in for another plaque collection and rinse with Chlorhexidine Oral Rinse for 30 seconds. After an elapsed time of 30 minutes subjects rinse with a 10% sucrose solution for 2 minutes, followed by plaque collection 8 minutes later. The process is repeated in 24 hours. The results show significantly less lactate produced in plaque that has been exposed to the chlorhexidine rinse ($p=0.002$ for Treatment 1 and $p=0.05$ for Treatment 2). The results validate the methodology for measuring lactate production and using it as a marker for acid production.

What is claimed is:

1. A method of measuring ammonia and/or calcium in a sample of dental plaque, comprising obtaining the sample, heating the sample sufficiently to kill bacteria and release ions into a solution, and measuring ammonium and/or calcium ions in the plaque using capillary electrophoresis.

2. The method of claim 1, further comprising the steps of
   a. obtaining a sample of plaque;
   b. diluting the sample with water;
   c. isolating the liquid fraction of the sample;
   d. combining the liquid fraction with
      i. an agent that allows electrophoretic separation of magnesium ions from calcium ions,
      ii. an agent that allows electrophoretic separation of potassium ions from ammonium ions, and
      iii. a buffer, comprising a basic agent and an acidic agent, which may be optionally the same as one of the agents i or ii allowing ion separation;
   e. passing the product of step d through a capillary tube, wherein there is an electric potential between one end of the capillary tube and the other sufficient to induce electrophoretic flow of ions through the tube;
   f. detecting ammonium ions and/or calcium ions in liquid that has passed through at least a portion of the capillary tube.

3. The method of claim 2 wherein in step d, the agent that allows separation of magnesium ions from calcium ions is selected from hydroxyisobutyric acid, lactic acid, malonic acid, and tartaric acid.

4. The method of claim 3 wherein in step d, the agent that allows separation of magnesium ions from calcium ions is hydroxyisobutyric acid.

5. The method of claim 2 wherein in step d, the agent that allows separation of potassium ions from ammonium ions is selected from neutral crown ethers and cyclofructans.

6. The method of claim 2 wherein in step d, the agent that that allows separation of potassium ions from ammonium ions is 18 crown 6 ether.

7. The method of claim 2 wherein in step d, the liquid fraction is combined with imidazole, hydroxyisobutyric acid, and 18 crown 6 ether.

8. The method of claim 2 wherein in step b the plaque is diluted to a concentration of about 0.01-0.1 mg plaque/mL water.

9. The method of claim 8 wherein the sample is heated to 60°-95° C.

10. The method of claim 9 wherein in step d, the agent that allows separation of magnesium ions from calcium ions is selected from hydroxyisobutyric acid, lactic acid, malonic acid, and tartaric acid.

11. The method of claim 10 wherein in step d, the agent that allows separation of magnesium ions from calcium ions is hydroxyisobutyric acid.

12. The method of claim 10 wherein in step d, the agent that allows separation of potassium ions from ammonium ions is selected from neutral crown ethers and cyclofructans.

13. The method of claim 12 wherein in step d, the agent that allows separation of potassium ions from ammonium ions is 18 crown 6 ether.

14. The method of claim 9 wherein in step d, the liquid fraction is combined with imidazole, hydroxyisobutyric acid, and 18 crown 6 ether.

15. The method of claim 1 wherein the sample is heated to 60°-95° C.

16. The method of claim 1 further comprising measuring acid in the plaque sample using capillary electrophoresis.

17. A method of measuring the relative population of arginolytic bacteria in plaque comprising measuring plaque ammonia production levels using the method of claim 1, and optionally additionally measuring plaque lactic acid levels to determine the relative population of cariogenic bacteria.

18. A method for assessing the efficacy of an oral care composition in promoting arginolytic bacteria and optionally inhibiting cariogenic bacteria comprising measuring ammonium levels in plaque using the method of claim 1.

* * * * *